US008304382B2

(12) United States Patent
Ferreira et al.

(10) Patent No.: US 8,304,382 B2
(45) Date of Patent: Nov. 6, 2012

(54) ANTI-INFLAMMATORY AND ANTI-ALLERGIC CYCLIC PEPTIDES

(75) Inventors: Mônica Ferreira, São Paulo (BR); Carla Silva, São Paulo (BR); Daniel Pimenta, São Paulo (BR); Fernanda Portaro, São Paulo (BR); Katia Conceição, São Paulo (BR); Marilene Demasi, São Paulo (BR)

(73) Assignees: Cristalia Productos Quimicos Farmaceuticos Ltda., Itapira (BR); Fundacao de Amparo a Pesquisa do Estado de Sao Paulo-FAPESP, Sau Paulo (BR)

( * ) Notice: Subject to any disclaimer, the term of this patent is extended or adjusted under 35 U.S.C. 154(b) by 76 days.

(21) Appl. No.: 12/374,287

(22) PCT Filed: Jul. 19, 2007

(86) PCT No.: PCT/BR2007/000186
§ 371 (c)(1),
(2), (4) Date: Feb. 10, 2009

(87) PCT Pub. No.: WO2008/009085
PCT Pub. Date: Jan. 24, 2008

(65) Prior Publication Data
US 2010/0144607 A1  Jun. 10, 2010

(30) Foreign Application Priority Data

Jul. 21, 2006  (BR) .................................. 0602885
Jul. 4, 2007   (BR) .................................. 0703175

(51) Int. Cl.
*A61K 38/00*  (2006.01)
*A61K 38/12*  (2006.01)
*C07K 5/00*   (2006.01)
*C07K 7/00*   (2006.01)
*C07K 16/00*  (2006.01)
*C07K 17/00*  (2006.01)

(52) U.S. Cl. .......................................... 514/1.1; 530/317
(58) Field of Classification Search .................. None
See application file for complete search history.

(56) References Cited

U.S. PATENT DOCUMENTS

| 5,290,762 A | 3/1994 | Lezdey et al. |
| 5,880,092 A * | 3/1999 | Pierschbacher et al. ..... 514/19.1 |
| 2003/0152564 A1 | 8/2003 | Fridkin et al. |
| 2003/0166003 A1 | 9/2003 | Cochran et al. |
| 2004/0254106 A1 * | 12/2004 | Carr et al. .................... 514/12 |
| 2007/0123455 A1 | 5/2007 | Palefsky et al. |

FOREIGN PATENT DOCUMENTS

| WO | WO 02/16409 | * | 2/2002 |
| WO | WO-03/070194 A2 | | 8/2003 |
| WO | WO-2004/068928 A2 | | 8/2004 |

OTHER PUBLICATIONS

Pierce et al. Identification of cyclized calmodulin antagonists from a phage display random peptide library. Molecular Diversity, 1995. vol. 1, pp. 259-265.*
Magalhaes et al. Natterins, a new class of proteins with kininogenase activity characterized from Thalassophryne nattereri fish venom. Biochimie. Aug. 2005. vol. 87, No. 8, pp. 687-699.*
Hruby. Designing Peptide Receptor Agonists and Antagonists. Nature Reviews. Drug Discovery. 2002. vol. 1, pp. 847-859.*
Palmblad et al. Oxidation of Methionine 35 Attenuates Formation of Amyloid beta-Peptide 1-40 Oligomers. The Journal of Biological Chemistry, 2002. Vo. 277, No. 22, pp. 19506-19510.*
Birk et al., "Separation of a Tribolium-protease inhibitor from soybeans on a calcium phosphate column", Biochem. Biophys. Acta., 1963, vol. 67, pp. 324-326.
Birk et al., "Isolation of Tribolium-proteolytic-enzyme-inhibitor from soybeans", Bull. Res. Counc. of Israel, 1962, vol. 11A, pp. 48-49.
Bowman, Donald E., "Differentiation of Soy Bean Antitryptic Factors", Proc. Soc. Expd. Med., 1946, vol. 63, pp. 547-550.
Magalhaes GS, Lopes-Ferreira M, Jungueira-de-Azevedo IL, Spencer PJ, Araujo MS, Portaro FC, Ma L, Valente RH, Juliano L, Fox JW, HoPJ, Moura-da-Silva AM. "Natterins, a new class of proteins with kininogenase activity characterized from Thalassophryne nattereri fish venom." Biochimie. Aug. 2005: 87 (8), pp. 687-699.

* cited by examiner

*Primary Examiner* — Marcela M Cordero Garcia
(74) *Attorney, Agent, or Firm* — Birch, Stewart, Kolasch & Birch, LLP (57) ABSTRACT

The present invention refers to synthetic, cyclic peptides containing a sequence of 13 L-amino acids in their primary structure which present anti-inflammatory and antiallergic activities, useful for the treatment of acute or chronic inflammation and/or allergies, being particularly useful for the treatment of acute or chronic allergic asthma. The invention also describes a pharmaceutical composition containing said peptides, its use and a method to treat or prevent acute and/or chronic inflammatory and/or allergic disorders.

15 Claims, 5 Drawing Sheets

SEQUENCE LISTING

<160> NUMBER OF SEQ ID NOS: 12

<210> SEQ ID NO 1
<211> LENGTH: 13
<212> TYPE: PRT
<213> ORGANISM: Artificial Sequence
<220> FEATURE:
<223> OTHER INFORMATION: Synthetic anti-inflamatory and antiallergic
      peptide

<400> SEQUENCE: 1

Ile Pro Arg Cys Arg Lys Met Pro Gly Val Lys Met Cys

-continued

```
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic anti-inflammatory and antiallergic
      peptide

<400> SEQUENCE: 2

Val Glu Gln Cys Thr Ile Ile Gly Asp Glu Lys Asp Cys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic anti-inflammatory and antiallergic
      peptide

<400> SEQUENCE: 3

Val Glu Gln Cys Thr Ile Ile Gly Asp Ala Lys Asp Cys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic anti-inflammatory and antiallergic
      peptide

<400> SEQUENCE: 4

Val Gln Gln Cys Ser Glu Ile Ala Gly Ala Lys Pro Cys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic anti-inflammatory and antiallergic
      peptide

<400> SEQUENCE: 5

Leu His Arg Cys Asp Lys Ile Ala Asp Ala Lys Pro Cys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic anti-inflammatory and antiallergic
      peptide

<400> SEQUENCE: 6

Ile Pro Arg Cys Arg Ala Met Pro Gly Val Lys Met Cys
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic anti-inflammatory and antiallergic
      peptide
```

```
<220> FEATURE:
<221> NAME/KEY: misc_feature
<222> LOCATION: (13)..(13)
<223> OTHER INFORMATION: 3' end contains NH2 - a carboxy terminal amide
      protecting group

<400> SEQUENCE: 7

Ile Pro Arg Cys Arg Lys Met Pro Gly Val Lys Met Cys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic anti-inflammatory and antiallergic
      peptide
<220> FEATURE:
<221> NAME/KEY: misc_feature
<222> LOCATION: (1)..(1)
<223> OTHER INFORMATION: 5' end contains an acetyl, amino terminal
      protecting group

<400> SEQUENCE: 8

Ile Pro Arg Cys Arg Lys Met Pro Gly Val Lys Met Cys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic anti-inflammatory and antiallergic
      peptide
<220> FEATURE:
<221> NAME/KEY: misc_feature
<222> LOCATION: (1)..(1)
<223> OTHER INFORMATION: 5' end contains an acetyl, amino terminal
      protecting group
<220> FEATURE:
<221> NAME/KEY: misc_feature
<222> LOCATION: (13)..(13)
<223> OTHER INFORMATION: 3' end contains NH2 - a carboxy terminal amide
      protecting group

<400> SEQUENCE: 9

Ile Pro Arg Cys Arg Lys Met Pro Gly Val Lys Met Cys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic anti-inflammatory and antiallergic
      peptide

<400> SEQUENCE: 10

Ile Pro Arg Cys Arg Lys Met Pro Gly Val Ala Met Cys
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: o-aminobenzoic acid (Abz) on 5' end and N-(2,
      4-dinitrophenyl) ethylenediamine (EDDnp) on 3' end; Abz and EDDnp
      are the fluorescent donor and acceptor groups, respectively
```

```
<400> SEQUENCE: 11

Phe Arg Ser Ser Arg Gln
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic anti-inflammatory and anti-allergic
      peptide

<400> SEQUENCE: 12

Cys Arg Lys Met Pro Gly Val Lys Met Cys
1               5                   10
```

ANTI-INFLAMMATORY AND ANTI-ALLERGIC CYCLIC PEPTIDES

This Application is the National Phase Under 35 U.S.C. §371 of PCT International Application No. PCT/BR2007/000186 which has an International filing date of Jul. 19, 2007, which claims priority to Brazilian Application No. PI0602885-3 filed on Jul. 21, 2006 and Brazilian Application No. PI0703175-0 filed on Jul. 4, 2007. The entire contents of all applications listed above are hereby incorporated by reference.

FIELD OF THE INVENTION

The present invention refers to synthetic, cyclic peptides containing a sequence of 13 L-amino acids in their primary structure which present anti-inflammatory and anti-allergic activities, useful for the treatment of acute or chronic inflammation and/or allergies, being particularly useful for the treatment of acute or chronic allergic asthma. The invention also describes a pharmaceutical composition containing said peptides, its use and a method to treat or prevent acute and/or chronic inflammatory and/or allergic disorders.

The following sequences will be used throughout the descriptive report:

| Sequence | |
|---|---|
| $Ile_1-Pro_2-Arg_3-Cys_4-Arg_5-Lys_6-Met_7-Pro_8-Gly_9-Val_{10}-Lys_{11}-Met_{12}-Cys_{13}$ | (SEQ ID NO: 1) |
| $Val_1-Glu_2-Gln_3-Cys_4-Thr_5-Ile_6-Ile_7-Gly_8-Asp_9-Glu_{10}-Lys_{11}-Asp_{12}-Cys_{13}$ | (SEQ ID NO: 2) |
| $Val_1-Glu_2-Gln_3-Cys_4-Thr_5-Ile_6-Ile_7-Gly_8-Asp_9-Ala_{10}-Lys_{11}-Asp_{12}-Cys_{13}$ | (SEQ ID NO: 3) |
| $Val_1-Gln_2-Gln_3-Cys_4-Ser_5-Glu_6-Ile_7-Ala_8-Gly_9-Ala_{10}-Lys_{11}-Pro_{12}-Cys_{13}$ | (SEQ ID NO: 4) |
| $Leu_1-His_2-Arg_3-Cys_4-Asp_5-Lys_6-Ile_7-Ala_8-Asp_9-Ala_{10}-Lys_{11}-Pro_{12}-Cys_{13}$ | (SEQ ID NO: 5) |
| $Ile_1-Pro_2-Arg_3-Cys_4-Arg_5-Ala_6-Met_7-Pro_8-Gly_9-Val_{10}-Lys_{11}-Met_{12}-Cys_{13}$ | (SEQ ID NO: 6) |
| $Ile_1-Pro_2-Arg_3-Cys_4-Arg_5-Lys_6-Met_7-Pro_8-Gly_9-Val_{10}-Lys_{11}-Met_{12}-Cys_{13}-NH_2$ | (SEQ ID NO: 7) |
| $Ac-Ile_1-Pro_2-Arg_3-Cys_4-Arg_5-Lys_6-Met_7-Pro_8-Gly_9-Val_{10}-Lys_{11}-Met_{12}-Cys_{13}$ | (SEQ ID NO: 8) |
| $Ac-Ile_1-Pro_2-Arg_3-Cys_4-Arg_5-Lys_6-Met_7-Pro_8-Gly_9-Val_{10}-Lys_{11}-Met_{12}-Cys_{13}-NH_2$ | (SEQ ID NO: 9) |
| $Ile_1-Pro_2-Arg_3-Cys_4-Arg_5-Lys_6-Met_7-Pro_8-Gly_9-Val_{10}-Ala_{11}-Met_{12}-Cys_{13}$ | (SEQ ID NO: 10) |
| Abz-Phe-Arg-Ser-Ser-Arg-Gln-EDDnp | (SEQ ID NO: 11) |
| $Cys_1-Arg_2-Lys_3-Met_4-Pro_5-Gly_6-Val_7-Lys_8-Met_9-Cys_{10}$ | (SEQ ID NO: 12) |

BASIS OF THE INVENTION

Inflammation is a dynamic and protective homeostatic response which occurs as a result of diverse aggressions to which the host is subjected. The acute phase of inflammation is characterized by alterations in the vascular system, which resulted in an increase in blood flow and structural changes in microcirculation, allowing an efflux of plasmatic proteins and leukocytes from circulation, what is accompanied by a series of events on cell and tissues aiming the homeostasis recovery.

In terms of events in the tissues, in this phase, leukocytes are recruited to the site of injury. Initially, the predominant influx is of neutrophils, followed by mononuclear cells. This influx is responsible for resolution of the inflammatory process, removing the aggressor agent and restoring tissue homeostasis.

Neutrophils are the first cells to reach the site of lesion and predominate numerically in the acute phase of tissue injury. They play an important role in defense of the organism by way of phagocytosis and destruction of the causative agent. In addition, neutrophils may be activated by cytokines produced by resident macrophages in endothelial cells and tissue.

Once blood monocytes leave the circulatory system and enter the site of injury, they differentiate into macrophages, which are the final effector cells in the inflammatory response. The macrophages are responsible for the phagocytosis of foreign particles and destroy them through the synthesis of reactive oxygen species such as nitric oxide. Sequentially, the activated macrophage acts by removing cellular debris, inducing the elimination of the antigen, and the resolution of the inflammatory response, as well as initiating the adaptive immune response.

Considering the cellular events in another way, leukocytes, which were recruited to the site of injury, initiate the process of secretion of pro-inflammatory or "alarm" cytokines (IL-1, TNF-α and IL-6) which initiate a chain of humoral and cellular reactions, at the site of inflammation as well as at distance.

Activation of stroma cells by the cytokines provoke the secretion of chemotactic chemokines which act upon neutrophils and mononuclear cells. At the inflammation site, vasodilation of the post-capillary venules initially occurs as well as changes in blood flow (a decrease), resulting in margination of the leukocytes along the vascular endothelium, a process mediated by selectins and their ligands, which are rich in carbohydrates.

After activation, the leukocyte stops rolling and firmly adheres to the endothelium. This event is a result of the binding of integrins β1 and β2 expressed in the leukocytes to various members of the immunoglobulins superfamily, expressed in the endothelium (ICAM-1, ICAM-2 and VCAM-1). Finally, the leukocytes migrate between the endothelial cells of the apical region towards the basolateral surface (diapedesis) in the direction of the extravascular space. The subsequent sub-endothelial migration through the extravascular tissue is dependent upon gradients of chemokines, chemotactic cytokines and adhesive interactions with the extracellular matrix. In the end, at the inflammatory focus, the leukocytes increase their cytotoxic functions, liberating oxidizing agents, proteases and other products such as growth factors and cytokines. Eosinophils, contrary to neutrophils, can survive in the tissues for long periods, at times for weeks, depending on the cytokines present in the micro-environment.

In relation to the cytokines involved in this process, pro-inflammatory cytokine TNF-α, produced by monocytes, macrophages, activated NK cells and T-lymphocytes, increases expression of adhesive molecules of the endothelial cells; activates neutrophils; stimulates macrophages to produce IL-1, IL-6, and IL-8; increases expression of class I MHC; increases the synthesis of prostaglandins by hypothalamus cells; acts on hepatocytes in the production of serum amyloid protein; suppresses division of cells in the medulla; reduces tissular perfusion (by diminishing myocardial contractility); relaxes vascular smooth muscle tonus and promotes intra-vascular thrombosis.

Cytokine IL-1, produced by macrophages, endothelial and epithelial cells, promotes the synthesis of IL-2 by T lymphocytes and the differentiation of B lymphocytes; promotes the synthesis of prostaglandins; increases the proliferation of T and B lymphocytes; acts upon macrophages inducing the synthesis of IL-1, IL-6, TNF-$\alpha$ and IL-8; promotes the acute phase synthesis of proteins; cachexia; and increases the division of cells in the medulla.

Cytokine IL-6, produced by macrophages, endothelial and T lymphocytes, acts in hepatocytes in the production of fibrinogen; growth factor for activated B lymphocytes; increases the division of cells in the medulla.

These cellular and tissular events result in effects that are characterized by pain, increase in body temperature, erythema, edema and loss of function near the injury site while inflammation persists. Failures in the regulation of inflammatory process control occur and can lead to epithelial, endothelial or muscle cell destruction as well as result in dysfunction at the cellular level or of the affected organ.

Asthma, for example, is a chronic, pulmonary inflammatory disease characterized by episodes of bronchoconstriction and by eosinophilic pulmonary inflammation. Bronchoconstriction, in the acute phase, is provoked by pharmacological mediators released by mast cells, activated by the binding of an allergen to allergen-specific IgE molecules on its surface, and the late phase bronchial reactivity is associated with a severe eosinophilic pulmonary inflammation. The T lymphocytes, principally subtype Th2, orchestrate these responses by way of production of cytokines such as IL-4, IL-5, IL-9 and IL-13 which are genetically controlled.

Presentation of the antigen by way of the mature pulmonary dendritic cells is the basis of the process of Th2 sensitization which occurs in allergic patients or in animals exposed to an airborne allergen.

Evidences of inflammation in asthma were initially derived from findings which showed the preferential accumulation of, T CD4$^+$ lymphocytes, type Th2, mast cells and macrophages in the lungs of patients with fatal asthma. Analysis of the bronchoalveolar lavage of asthmatic patients during late phase reactions, LPR, also revealed the presence of an elevated number of T CD4$^+$ lymphocytes and eosinophils.

Activated T CD4$^+$ cells are the principal source of cytokines (IL-4, IL-5, IL-9 and IL-13) which are responsible for the development of an allergic pulmonary inflammatory response, typically Th2, with predominance of an eosinophilic infiltrate and production of IgE. The eosinophils are attracted to the lung due to the action of diverse factors such as cytokines and chemokines which promote chemotaxy, the increase in the expression of adhesive molecules in the vascular endothelium and at the cell surface, activation and cellular transmigration.

Once activated, the eosinoplhils release their granular contents (principal basic protein, neurotoxin derived from eosinoplhils, cationic protein from eosinoplhils and eosinophil generated peroxidase), which, in addition to being toxic to helminthes and bacteria, directly stimulate the smooth bronchial musculature, causing contraction and promoting the increased reactivity towards cholinergic mediators.

In a previously established pulmonary inflammation, eosinoplhils are capable of amplifying the response, recruiting new cells, due to the localized production of pro-inflammatory cytokines. Chronic eosinophilic inflammation and IgE antibodies have been directly associated with the severity of the asthma.

Chronic inflammation in asthma is accompanied by pulmonary hyper-reactivity (increased bronchoconstriction in response to non-specific stimuli) and by structural changes in the aerial passages.

Many factors can precipitate an asthma attack, including allergens, bacterial or viral infections, exercise, abrupt meteorological changes, or exposure to airborne irritants, such as tobacco smoke. The principal causes of asthma in children under 5 are viral infections caused by parainfluenza virus (PIV), syncytial respiratory virus (VSR), rhinovirus and enterovirus.

Sensitive asthmatic individuals, when exposed to an allergen in aerosol form, manifest symptoms which begin within 5 to 10 minutes. During this immediate phase of asthma, the following symptoms are observed: contraction of the smooth bronchial musculature, localized edema, increase in the secretion of mucus by the epithelial bronchial glands and a slight cellular infiltration. These characteristics can be explained by the action of mediators such as histamine, prostaglandin D2 (PGD2), leukotriene C4 (LTC4), platelet activating factor (PAF) and cytokines TNF-$\alpha$ and IL-1 released by mast cells activated by IgE allergen-specific antibodies.

According to estimates by the National Center for Health Statistics of the Center for the Control and Prevention of Diseases (NCHS-CDC, 2005, Hyattsville, Md.) approximately 22.2 million people suffer from asthma in the United States, among which 6.5 million are less than 18 years old. In the United States alone, close to 11 people die from asthma per day. In Brazil, estimates show that 10% of the population presents symptoms of asthma, with 2500 deaths per year, being the fourth largest cause for admission to the Universal Health Care System (SUS). Among asthmatic patients, 60% of the cases are difficult to control.

Currently, treatments for inflammation and asthma utilize two categories of drugs: 1) pharmaceutical agents to improve acute symptoms (60% of asthmatics) represented principally by $\beta_2$-agonists with a rapid onset of action, ipratropium bromide which is a quaternary ammonium anti-cholinergic agent and aminophylline, a xanthine derivative which causes relaxation of the smooth muscle of the bronchioles; and 2) maintenance drugs, used to prevent the symptoms of asthma, represented principally by inhaled and systemic corticosteroids.

Nonetheless, use of these drugs, especially repeated or prolonged use, have limitations due to their non-specific action and consequent undesirable side effects for the patients. Furthermore, anti-inflammatory medications currently in use are not able to significantly prevent the loss of pulmonary function associated with asthma.

Drugs which seek to treat inflammation with the potential of minimizing the risk of side effects and which are more specific are being constantly investigated. Several examples may be cited.

Patent application WO 03/070194 presents a proposal to esterify corticosteroids with $\alpha$-amino acids, thus being able to function as pro-drugs useful for the treatment of rhinitis and asthma, particularly by way of inhalation, and for the treatment of inflammation, particularly by way of local or topical administration. However, the advantage presented by the proposed pro-drugs is not clear as the proposed treatment still depends upon the action of corticosteroids.

Patent application WO 2004/068928 refers to peptides isolated from the defensive secretion from the skin of the toad, Bombina maxima, which are agonists of the $B_2$ bradykinin receptor able to be used to treat and/or prevent disorders associated with bradykinin including cardiovascular disorders, inflammation, asthma, allergic rhinitis, pain, angiogenesis among others.

In yet another patent application, US 2003/0152564, a peptide is presented which corresponds to positions 62-71 of the sequence of human C-reative protein which is able to inhibit, in vitro, enzymatic activity of human leucocitary elastase and/or of human cathepsin G, being able to be destined toward the treatment of chronic inflammatory conditions such as rheumatoid arthritis, pulmonary emphysema, cystic fibrosis, bronchitis, asthma and some acute syndromes involving respiratory disturbances.

Patent application US 2007/0123455 proposes a method and compositions which comprise the human proteins S100A8 and/or S100A9, said to be adequate to treat inflammatory disorders such as allergies, asthma, atherosclerosis, auto-immune diseases, infections, among others.

U.S. Pat. No. 5,290,762 describes a method for prophylaxis or treatment of inflammatory diseases in a patient which comprises the administration to the location of injury, of a quantity of at least one inhibitor of serine protease. The patent document claims, as a group of serine protease inhibitors, any inhibitor of the secretion of leucocytic protease, C-reactive protein, serum amyloid protein A, alpha-2-macroglobulin or alpha-2-antiplasmin.

The involvement of the inhibition of serine protease for the treatment of inflammation has been widely investigated. For example, human tryptase is a serine protease, found in the mast cells, similar to trypsin. The tryptase is the mediator of a series of allergic and inflammatory pathologies, including rhinitis, conjunctivitis and asthma. As such, inhibitors of this serine protease could be utilized with success for the treatment of allergic and respiratory diseases.

Among the inhibitors of serine protease, the best studied are the peptides described by Bowman [*Proc. Soc. Expd. Med.* 1946 63:547] and Birk et. al. [*Bull. Res. Council Israel, Sec A* 1962 11:48; *Biochem. Biophys. Acta* 1963 67:326] (which are the origin of the denomination BBI—Bowman Birk Inhibitors—originated). BBI's are encountered abundantly in dicotyledonous and monocotyledonous plants. Among these, the named SFTI-1 (sunflower trypsin inhibitor-1) is pointed out, which is a bicyclic peptide composed of 14 amino acids, up to the present, is the smallest and most potent natural Bowman-Birk type inhibitor. SFTI-1 has been used in transgenic plants against pathogens and insects, but may also be utilized in the prevention of cancer, dengue fever and other inflammatory and allergic diseases.

In addition to pharmacologically active peptides can be produced by plants, substances produced by animals, for example, venoms, have also been the targets of investigation. Animal toxins may be considered to be molecules developed by nature capable of reaching specific and selective targets, inhibiting or stimulating physiological reactions.

Particularly, the proteins denominated natterins, which are isolated from the venom of the fish *Thalassophryne nattereri* found in Brazil, should be pointed out. These proteins form a family of toxins with a molecular mass around 38 kna, whose sequences present a high degree of homology among them and are capable of inducing innumerous biological activities such as edema and nociception.

Using the natterins as a starting point, it could be observed sequences of amino acids which are not obtained per se by way of purification of the natural venom, although stand out with respect to their structural similarity to the Bowman-Birk peptides. Attempts to isolate said sequences of amino acids from the natterins are frustrated, since it requires a long and laborious process, resulting in very small quantities of impure peptide fragments, not exactly correspondent to the peptides of interest of the present invention. This is a significant impediment to the industrial production of these peptides.

SUMMARY OF THE INVENTION

The present invention presents cyclic peptides obtained by artificial peptide synthesis comprising a sequence of 13 L-amino acids in their primary structure, presenting specifically the amino acid cysteine in positions 4 and 13 of the peptide chain and the amino acid lysine in position 11 of the peptide chain, in that they are characterized by containing a disulfide bridge formed between the thiol groups of the 4 and 13 cysteine residues, forming a cyclic peptide. Said synthetic, cyclic peptides present anti-inflammatory and anti-allergic activity, particularly with potential application in the treatment of acute and/or chronic asthma.

DETAILED DESCRIPTION OF THE INVENTION

The present invention refers to cyclic, synthetic peptides comprising a sequence of 13 L-amino acids in their primary structure, presenting, preferably, chemical protecting groups at one or both of the extremities of the peptide, said peptides presenting anti-inflammatory and anti-allergic activities.

The peptides of the present invention possess the amino acid cysteine at the positions 4 and 13 of the peptide chain and the amino acid lysine at the position 11 of the peptide chain.

Additionally, the peptides included in the present invention preferably possess the amino acids valine, leucine or isoleucine or another hydrophobic and neutral amino acid at position 1 of their basic sequence.

Additionally, the peptides included in the present invention preferably possess the amino acids arginine, glutamine or another hydrophilic and polar amino acid, capable of possessing a positive charge, at position 3 of their basic sequence.

Additionally, the peptides included in the present invention preferably possess the amino acids arginine, threonine, serine, aspartate or another hydrophilic and polar amino acid at position 5 of their basic sequence.

Additionally, the peptides included in the present invention preferably possess the amino acids methionine, isoleucine, leucine or another hydrophilic and neutral amino acid at position 7 of their basic sequence.

Additionally, the peptides included in the present invention preferably possess the amino acids glycine or aspartate at position 9 of their basic sequence.

Particularly, the peptides of the present invention are characterized by the fact that they contain a disulfide bridge formed between the thiol groups of the 4 and 13 cysteine residues, forming a cyclic peptide.

Chemical protection of the peptide molecule may be accomplished by the addition of chemical protecting groups to the carboxy terminal extremity of the peptide, or at the amino terminal extremity of the peptide, or yet still by the protection of both the extremities of the molecule. Preferably, protection of the molecule occurs by way of amidation of the carboxyl group of the amino acid cysteine at position 13 of the peptides of the present invention, or by way of acetylation of the amino acid residue at position 1 of the peptide chain, or still, by protection of both the carboxy terminal and the amino terminal extremities.

In the main embodiment of the present invention, the peptides are characterized by the sequences of amino acids identified in this document by way of the SEQ ID NOs: 1-9 also being included within the scope of this invention their derivatives, homologues, analogues and/or mimetics of the same.

Also included within the scope of the present invention are substitutions, deletions or modifications of the amino acid sequence in the peptides which will be obvious to one skilled in the art from the peptides herein taught. Examples of these modifications include, but are not limited to: the individual, alternate or combined substitution of praline residues by hydroxylated proline (hydroxyproline); the individual, alternate or combined substitution of methionine residues by an oxidized form of methionine; and the individual, alternate or combined substitution of L-amino acids by D-amino acids.

Also included within the scope of the present invention are larger peptides which contain in their basic sequence, the sequences of amino acids herein described. Similarly, peptides to which deletions of amino acids at positions 1, 2 and 3 have been made, as described herein, while still maintaining unaltered the cyclic structure which occurs between the amino acids at positions 4 to 13, are also included within the scope of the present invention.

The cyclic peptides included in the present invention, alone, or in a combination containing at least two of the peptides, present the capacity to inhibit the adhesion and rolling of leukocytes in mammals tested in the laboratory. In addition to the inhibition of adhesion and rolling of the leukocytes, there is also observed a decrease in, and a prevention of the recruiting of leukocytes, particularly neutrophils and macrophages, in the peritoneal cavity of laboratory mammals injected with the inflammatory agent LPS (lipopolysaccharide), when treated with representative peptides of the present invention.

In immunized mammals challenged with ovalbumin (OVA), which causes the manifestation of acute murine asthma, the cyclic peptides of the present invention, alone or in a combination containing at least two of the peptides, when administrated intramuscularly, intranasally and orally, have also been shown capable of inhibiting the recruitment of the total number of leukocytes toward the alveolar space, this decrease being characterized particularly by the absence of eosinophils in the bronchoalveolar lavage.

The cyclic peptides of the present invention, alone or in a combination containing at least two of the peptides, are also able to reduce the total number of leukocytes recruited to the alveolar space, with a reduction in eosinophils, in a conventional experimental model for the development of chronic asthma in animals.

In light of the characteristics heretofore related, it has been observed that the cyclic peptides of the present invention, alone or in a combination containing at least two of the peptides, are capable of inhibiting, in mammals, inflammatory manifestations, pathological allergic manifestations where an influx of eosinophils is observed such as asthma, bronchitis, rhinitis and dermatitis, in addition to associated pathological manifestations such as arthritis, disturbances of the immune system, lymphocytic dysfunction during the immune response, tumors, cellular adhesion and/or manifestations of parasitic diseases. The results obtained for asthma were compared with the conventional treatment for asthma, utilizing dexamethasone, in which the peptides of the present invention were shown to be equally efficient.

Additionally, it has been observed that the cyclic peptides of the present invention are resistant to digestion with trypsin, thus being able to be administered orally. Other means of administration which may be employed for the peptides of the present invention include, but are not limited to, intranasal, intramuscular and intravenous administration.

In addition to being resistant to the action of the enzyme trypsin, the peptides of the present invention are also able to inhibit the proteolytic action of trypsin, presenting a $K_i$ in the range of 20 to 63.6 nM. This property of the peptides of the present invention suggests that such peptides may be classified as inhibitors of serine protease, once trypsin is an important enzyme representative of the family of serine proteases. Knowing also that human tryptase is a serine protease found in the mast cells, being very similar to trypsin, and that its inhibition has shown to be successful in the treatment of respiratory and allergic diseases, it can be suggested that the activity verified for the peptides of the present invention is related to the inhibition of serine proteases.

The peptides of the present invention do not possess any cytotoxic effect on macrophages, and also do not demonstrate any damaging effect on muscular fibers or on microcirculation in the cremaster muscle of laboratory animals.

Furthermore, the peptides of the present invention, alone or in combination, have not been shown to be immunogenic, in that they do not induce the synthesis of specific antibodies and, above all, have not been shown to be lethal.

In one embodiment of the present invention, the cyclic peptides as set forth on SEQ ID NOs: 1-9—may be obtained employing known techniques for the synthesis of peptides, such as classical chemical synthesis in solution or in the solid phase; enzymatic synthesis; or by way of techniques using recombinant DNA.

The chemical synthesis of the cyclic peptides of the present invention may be preferably accomplished in the solid phase, and more preferably, with use of the FMOC (9-Fluorenyl-methoxycarbonyl) strategy to protect the alpha-amino groups present in the reaction.

The purification of the synthetic peptides may be accomplished employing chromatographic techniques, well known in the state of the art. Preferably, liquid chromatography is employed, the purity and identity of the peptides being confirmed by mass spectrometry.

After purification of the synthesized peptides according to the above description, it is then necessary to introduce the disulfide bridges into the respective peptides. The disulfide bridges are formed between cysteine residues at positions 4 and 13 in the same peptide chain by the method of reduction in air, for example, by dissolving the peptide in a solution of 0.01 to 0.5M ammonium bicarbonate in a proportion of 0.05 to 15 mg/mL with agitation until complete formation of the disulfide bridge. The peptides may be isolated by lyophilization and purified by way of preparative liquid chromatography.

Another embodiment of present invention refers to a pharmaceutical composition containing the peptides as set forth on SEQ ID NOs: 1-9, their derivatives, homologues, analogues and/or mimetics, which may be in the form of pharmaceutically acceptable salts of the same, alone or in a combination containing at least two of the peptides, in one or more vehicles chosen among a diluent, an excipient or a pharmaceutically acceptable solvent.

Another embodiment of the present invention is a method to treat or prevent inflammatory and/or allergic disorders, acute or chronic, such as, but not limited to, bronchial asthma, rhinitis, arthritis, atopic dermatitis, disturbances of the immune system, lymphocytic dysfunction during the immune response, tumors, cellular adhesion and/or manifestations of parasitic diseases, by way of administration, to a mammal, the cyclic peptides as set forth on SEQ ID NOs: 1-9, alone or in combination, or of pharmaceutical compositions containing at least one of the peptides of the present invention.

Yet another embodiment of the present invention is the use of the cyclic peptides as set forth on SEQ ID NOs: 1-9, alone or in a combination containing at least two of the peptides, in the manufacture of medicines employed in the prevention or treatment of inflammatory and/or allergic disorders, acute or chronic, such as, but not limited to, bronchial asthma, rhinitis, arthritis, atopic dermatitis, disturbances of the immune system, lymphocytic dysfunction during the immune response, tumors, cellular adhesion and/or manifestations of parasitic diseases. According to this aspect, the synthetic, cyclic peptides of the present invention, alone or in combination, may be used to obtain a pro-drug or drug which inhibits the development of inflammatory and/or allergic conditions in mammals.

The administration of the cyclic peptides of the present invention or of pharmaceutical compositions containing the same, may be accomplished by way of, but not limited to, intramuscular, intranasal, intravenous and oral administration, the preferred method of administration being orally.

The following examples are cited to illustrate the embodiments of the present invention and must be employed only for a better comprehension of the developments contained at the present invention but should not be construed as to limit the scope or spirit of the invention.

Example 1A

Inhibition of Trypsin

Figure 1:
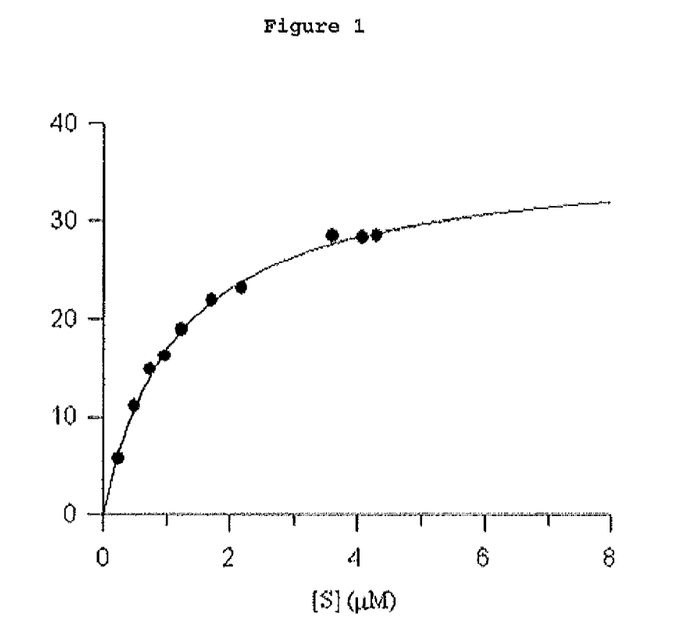
FIG. 1: Michaelis-Menten kinetics obtained for the hydrolysis of the substrate Abz-Phe-Arg-Ser-Ser-Arg-Gln-EDDnp (SEQ ID NO: 11) by the catalytic activity of trypsin.

Studies on the inhibition of trypsin with peptide SEQ ID NO: 1 revealed a simple, competitive inhibition, as shown in FIG. 1 (simple intercept with the X axis) and yielded a value of $K_i$ in the range of 10 µM-0.1 nM.

The substrate utilized was Abz-Phe-Arg-Ser-Ser-Arg-Gln-EDDnp (SEQ ID NO: 11), a fluorescent analog of bradykinin, purified by way of high pressure liquid chromatography, (HPLC) until purity greater than 95% (single peak) was achieved.

Example 1B

Tests a) Enzymatic Reactions for the Determination of $K_m$ and $k_{cat}$

The concentration of the substrate solution was determined by fluorometric analysis of the product Abz formed after complete hydrolysis by trypsin.

The hydrolysis reactions were conducted using a Hitachi. F-2000 spectrofluorometer, with the excitation and emission slits set at 10 and 20 nm, and the excitation and emission wavelengths at 320 and 420 nm, respectively. The temperature of the reaction cuvette was maintained at 37° C. in a thermostatically controlled compartment.

The enzymatic activity of trypsin (0.5-5 nM) was determined in 50 mM Tris-HCl buffer, pH 8.0, containing 20 mM NaCl at 37° C., with the addition of approximately 0.1-6.0 µM of the fluorescent substrates. The increase in fluorescence was monitored continually for 5 min in the spectrofluorometer. When necessary, the correction of the fluorescent reading was done using the empiric equation described by Araújo et. al., Biochemistry 25; 8519, 2000. Kinetic data were determined from the initial hydrolysis (consumption of substrate less than 10%) and calculations involving kinetic parameters ($K_m$, $V_{máx}$ and $k_{cat}$) were performed using the Michaelis-Menten equation furnished by the GRAFIT for Windows 3.0 program.

b) Determination of the Inhibition Constants ($K_i$)

To determine the inhibition kinetics of trypsin with the peptides of the present invention, three substrate concentrations were used: a) corresponding to half of the value of $K_m$ (0.8 µM); b) corresponding to the whole value of $K_m$ (1.6 µM); c) corresponding to slightly more than double the value of $K_m$ (3.5 µM). The enzyme was employed at a concentration of 3.0 nM and the inhibitors (SEQ ID NO: 1 to SEQ ID NO: 9) at three concentrations (10 nM, 100 nM and 1 µM), in addition to a control for each substrate concentration, the substrate consumption being less than 10% of the initial concentration. Incubation carried out at 37° C. Tris-HCl buffer, pH 8.0, containing 20 mM NaCl at 37° C. For characterization of enzymatic inhibition, a Lineweaver-Burk plot was employed (1/V vs 1/S), and the value of $K_i$ was determined from the relation between the apparent inhibition constant ($K_{i(app)}$) and the value of $K_m$ for the substrate: $K_{i(app)} = [I]/[(v_0/v_i)-1]$ and $K_i = K_{i(app)}/[(K_m/[S])+1]$ where; [I]=inhibitor concentration; ($v_0/v_i$)=ratio of the hydrolysis velocities in the absence and presence of inhibitor, respectively. $K_m/[S]$=ratio between $K_m$ of the substrate and substrate concentration.

The results obtained are summarized in table 1 below:

TABLE 1

| Identifying Sequence | Ki (nM) | |
|---|---|---|
| SEQ ID NO: 1 | 22.5 | |
| SEQ ID NO: 2 | 24.0 | |
| SEQ ID NO: 3 | 63.6 | |
| SEQ ID NO: 4 | 42.0 | 44.0 |

TABLE 1-continued

| Identifying Sequence | Ki (nM) |
|---|---|
| SEQ ID NO: 6 | 24.2 |
| SEQ ID NO: 7 | 20.0 |
| SEQ ID NO: 8 | 24.8 |
| SEQ ID NO: 9 | 21.8 |

Example 2

Inhibition of Adhesion and Rolling of Leukocytes In Vivo a) Rolling of Leukocytes for the Peptides of the Present Invention:

The test to verify the inhibition of adhesion and rolling of leukocytes was performed in mice (n=3/per group), which were anaesthetized with sodium pentobarbital (Hypnol°, 50 mg/Kg) and maintained under a temperature controlled plate (37° C.). Surgical manipulation of the scrotal sac was performed to expose the cremaster muscle, which was fixed around a transparent area of the plate. This was positioned over the chariot of the optical microscope to permit in vivo visualization of the local microcirculation. The preparations were maintained humid and warmed by irrigation with 0.15 M PBS (phosphate buffer solution). The inflammatory agent LPS (lipopolysaccharide), at a concentration of 1 μg/mL, diluted to 20 μL, was topically applied to the cremaster muscle. The aspect of the post-capillary venule was registered before and after the application of the LPS (lipopolysaccharide). The peptides SEQ ID NO: 1 to SEQ ID NO: 9 (1 μM) were applied topically 15 min after application of the LPS. The pre and post-capillary venules, arterioles and muscular fibers events were observed for 30 minutes. The rolling of the leukocytes, the firm adherence and the leakage at the post-capillary venules between 20-40 μm in diameter were registered and quantified in 1 minute intervals for a period of 10 minutes. Transmigration was defined as the number of leukocytes in the extravascular tissue over a segment extending 100 μm. Microcirculation of the cremaster was analyzed by the epi-illumination technique using an intra-vital fluorescence microscope (Axio Imager A1, Carl Zeiss, Germany) as described by Sperandio et. al. (J. Exp. Med., 19; 197(10): 1355-1363, 2003).

Figure 2:
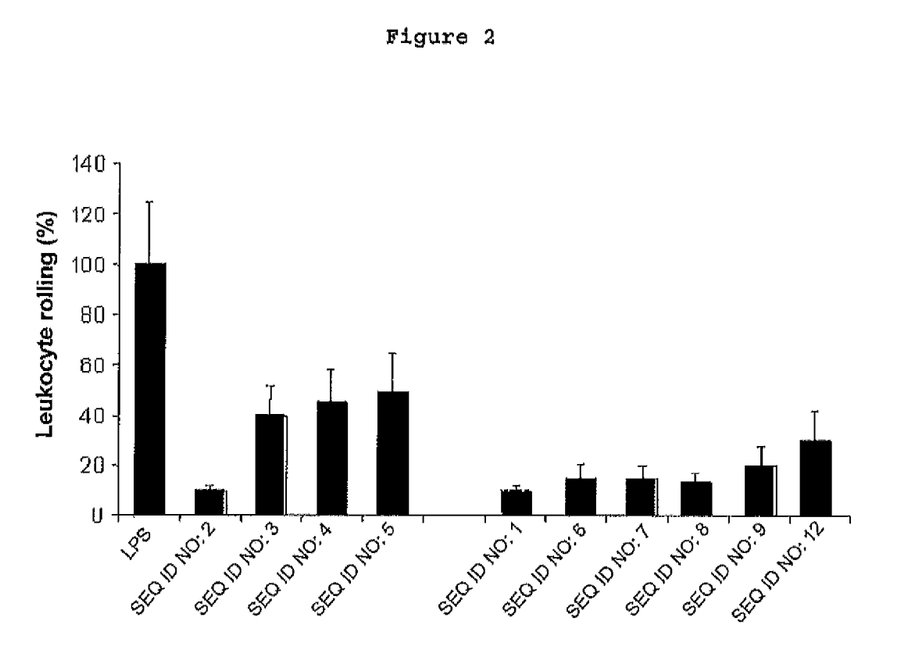
FIG. 2: Effect of the different peptide sequences on leucocyte rolling induced in the microcirculation by LPS (lipopolysaccharide). *$p<0.05$ compared with the LPS group.

The peptides tested induced a decrease in the rolling of the leukocytes in the post-capillary venules of the cremaster muscle of mice on the order of 50 to 90%, as can be seen in FIG. 2.

b) Rolling of Leukocytes with a Modified Peptide: Deletion of the Amino Acids at Positions 1, 2 and 3.

Figure 3:
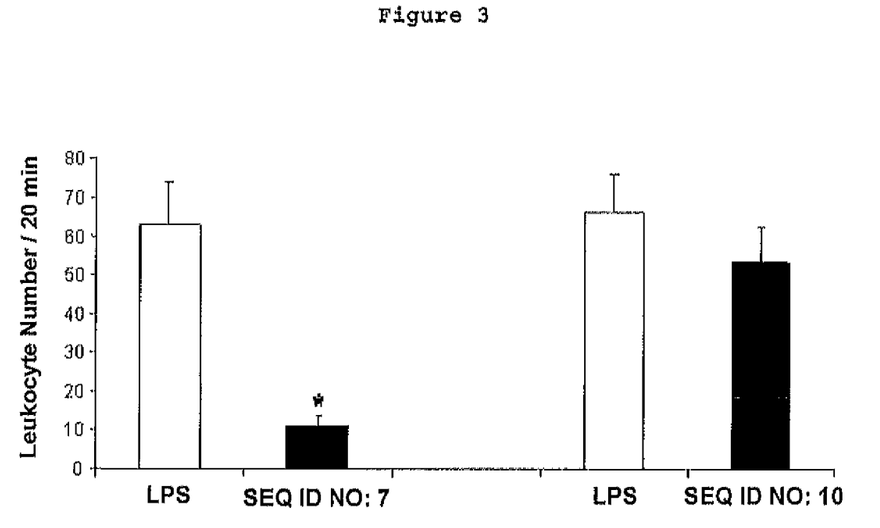
FIG. 3: Effect of the change in essential amino acid in the sequence SEQ ID NO: 1, SEQ ID NO: 10, on the rolling of leukocytes induced in the microcirculation by LPS (lipopolysaccharide) in comparison with SEQ ID NO: 7. *$p<0.05$ compared with the LPS group.

The test above was repeated with a modified peptide SEQ ID NO: 12 as represented below:

SEQ ID NO: 1    $Ile_1\text{-}Pro_2\text{-}Arg_3\text{-}Cys_4\text{-}Arg_5\text{-}Lys_6\text{-}Met_7\text{-}Pro_8\text{-}Gly_9\text{-}Val_{10}\text{-}Lys_{11}\text{-}Met_{12}\text{-}Cys_{13}$ SEQ ID NO: 12   $Cys_1\text{-}Arg_2\text{-}Lys_3\text{-}Met_4\text{-}Pro_5\text{-}Gly_6\text{-}Val_7\text{-}Lys_8\text{-}Met_9\text{-}Cys_{10}$ This modification had as objective to verify the need of the cyclic structure resulting from the disulfide bridge between the thiol groups present in the cysteine residues at positions 4 and 13 for anti-inflammatory activity of the peptides of the present invention. The peptide from which the amino acids had been removed maintained inhibitory activity with respect to the rolling of leukocytes in comparison to the peptides described in the present invention, as can be seen in FIG. 2.

c) Effect of the Substitution of Lys at Position 11 on the Activity of the Peptides of the Present Invention The test for leucocyte rolling was repeated, as described in example 2, for a modified peptide ($Mod_{Lys/Ala}$) in which lysine at position 11 of one of the peptides of the present invention was substituted by alanine (an amino acid with properties contrary to lysine) to determine the essentiality of the $Lys_{11}$ residue for the activity of the peptides of the present invention as is represented below:

Seq01    $Ile_1\text{-}Pro_2\text{-}Arg_3\text{-}Cys_4\text{-}Arg_5\text{-}Lys_6\text{-}Met_7\text{-}Pro_8\text{-}Gly_9\text{-}Val_{10}\text{-}Lys_{11}\text{-}Met_{12}\text{-}Cys_{13}$ $Mod_{Lys/Ala}$ (SEQ ID NO: 10)    $Ile_1\text{-}Pro_2\text{-}Arg_3\text{-}Cys_4\text{-}Arg_5\text{-}Lys_6\text{-}Met_7\text{-}Pro_8\text{-}Gly_9\text{-}Val_{10}\text{-}Ala_{11}\text{-}Met_{12}\text{-}Cys_{13}$ The modified peptide, SEQ ID NO: 10, was not efficient in the inhibition of leucocyte rolling when compared to peptide as set forth on SEQ ID NO: 7, as can be seen in FIG. 3, which demonstrates the importance of the presence of $Lys_{11}$ to maintain pharmacological activity.

Example 3

Prevention of Peritonitis Induced by LPS

Mice were injected intraperitoneally with 4 nmol or 40 nmol of the peptide identified by SEQ ID NO: 7 dissolved in 500 µL of sterile saline solution, 30 minutes prior to administering intraperitoneal injection of LPS (O55:BR 20 µg/mL, Sigma) diluted in 500 µL of sterile saline solution. Animals injected only with sterile saline were considered controls, 24 h after injection of LPS, the animals were sacrificed with a high dose of chloral hydrate to obtain the washing of the peritoneal cavity to count the number of cells (A), neutrophils (B) and macrophages (C). The material removed from the peritoneum was centrifuged for 10 minutes at 1500 rpm and 4° C., the supernatant was separated and frozen at −20° C. for future analyses, while the remaining material containing the cells was re-suspended in PBS 0.1% BSA. The total count was performed in a Neubauer chamber, For the differential count, an aliquot of the cellular suspension was placed on slides and centrifuged (Citospin), stained with Hema 3 and examined under the optical microscope, counting a total of 300 cells. The absolute number of each cellular population was obtained by multiplication of the percentages by the total number of cells found in the sample volume.

Figure 4:
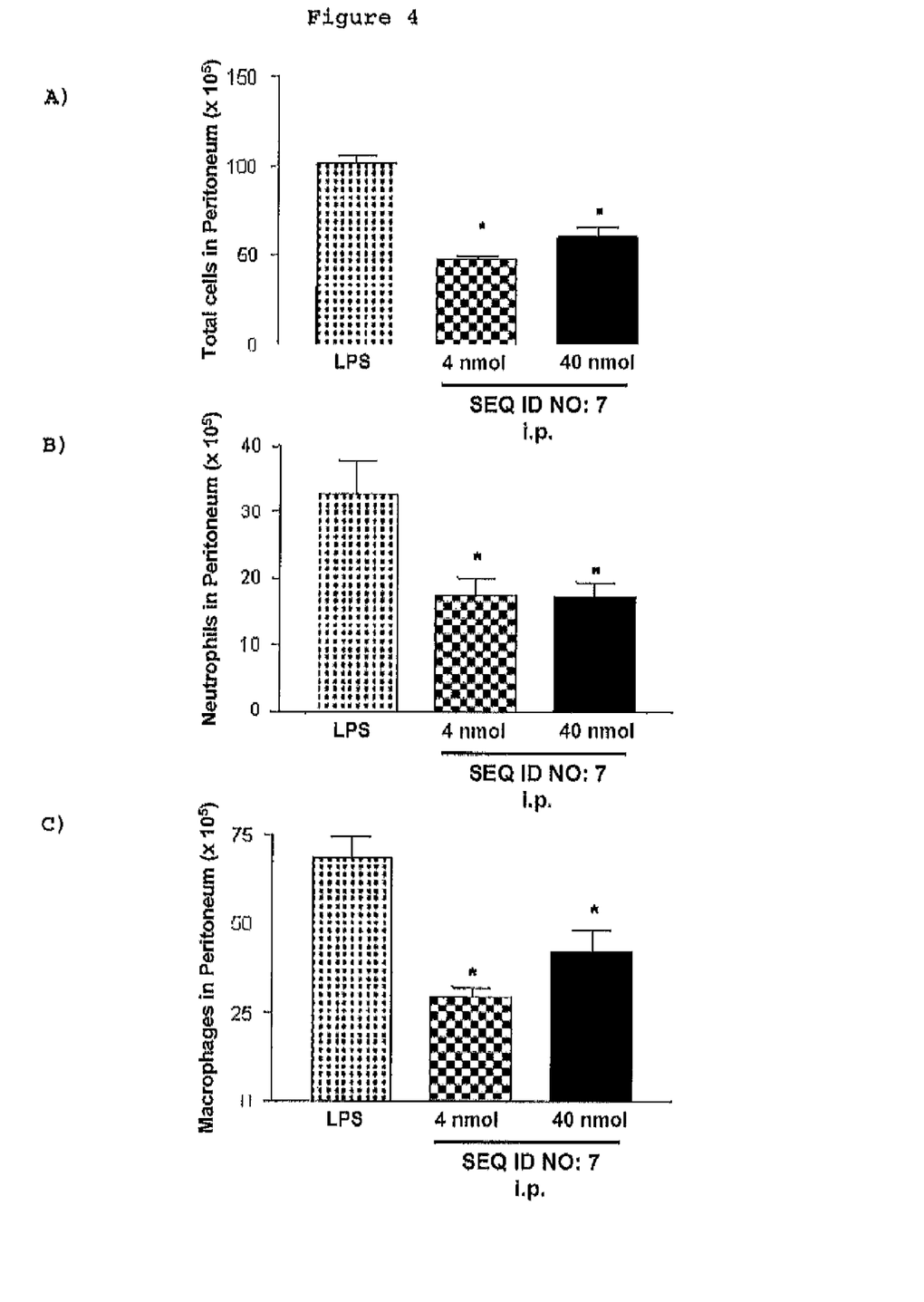
FIG. 4: Prevention of LPS (lipopolysaccharide) induced peritonitis by SEQ ID NO: 7. Mice injected with LPS (10 μg/mL) were treated intraperitoneally 30 minutes before with SEQ ID NO: 7 (4 or 40 nM). The figure represents the total number of cells (A), neutrophils (B) and macrophages (C) of the peritoneal washing after 24 hours. The results are expressed as the median±SEM. *$p<0.05$ compared to the LPS group.

Both concentrations of the peptide tested (4 nmol and nmol) prevented close to 50% of the recruitment of leukocytes in the peritoneal cavity of mice injected with LPS (compared to the control). It can also be verified by examining FIG. 4, that the peptide prevented the recruitment of neutrophils and macrophages.

Example 4

Inhibition of the Acute and Chronic Pulmonary Allergic and Inflammatory Response Induction of acute pulmonary asthma was observed in BALB/c mice, 7 week old, males, which were immunized with 1% ovalbumin (OVA grade V, 10 µg, Sigma) adsorbed on 1.6 mg of aluminum hydroxide on days 0 and 7. After the $14^{th}$ day, the animals were submitted to 3 challenges per week with a 1% OVA aerosol, Immunized animals and challenged only with PBS (phosphate buffered saline) were considered controls. To induce chronic asthma, the animals were challenged 3 times a week during 3 consecutive weeks.

For the aerosol challenge, the animals were placed in a closed plastic box adapted with an ultra-sonic nebulizer (US-800, ICEL) and exposed to inhalation of 2 mL of a 1% solution of ovalbumin (grade V, Sigma) in saline, over 20 minutes, 24 h after the last aerosol challenge, the animals were sacrificed with a high dose of chloral hydrate to obtain the peripheral blood, the Broncho-Alveolar Lavage (BAL) and the pulmonary tissue to count the total number of leukocytes and eosinophils.

Groups of animals were treated with 4 nmol or 40 nmol of the peptide identified by SEQ ID NO: 7 intranasally and intraperitoneally 30 minutes before each challenge, and orally 1 hour before each challenge. The group of animals with chronic asthma was treated only with 4 nmol or 40 nmol of the peptide identified by SEQ ID NO: 7_intraperitoneally 30 minutes before each challenge.

To obtain the BAL, the animals of both groups (OVA treated or Control) were sacrificed with 10% chloral hydrate, the blood removed, and had a cannula placed in the trachea. The aerial space was washed with three, 1 mL aliquots of HBSS (Hanks Balanced Salt Solution) EDTA (ethylenediaminetetraacetic acid). After collection, the BAL was immediately centrifuged at 800 rpm for 10 minutes, the supernatant discarded, and the cellular button was re-suspended in 1 mL of HBSS 0.1% BSA (bovine serum albumin) to count the cells. The total cells from the BAL were counted in a Neubauer chamber. Aliquots containing $5 \times 10^5$ cells were centrifuged on glass slides using a cytocentrifuge, for 5 minutes at 600 rpm. To determine the percentages of the different cellular populations, the slides were stained with Hema 3 and 300 cells were counted in randomly selected fields. The absolute number of each cellular population in the BAL was obtained by multiplication of the percentages by the total number of cells found in the sample volume.

Figure 5:
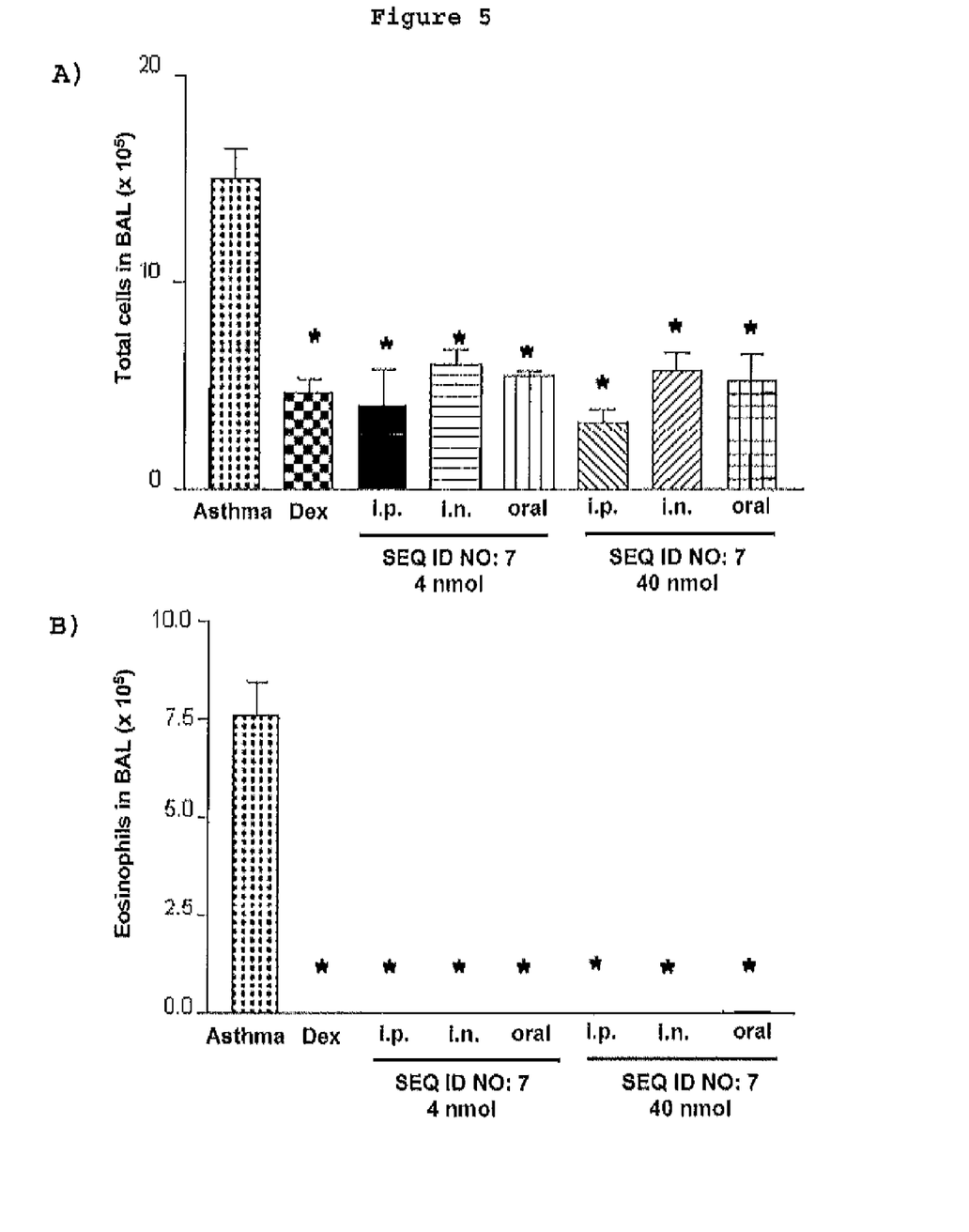
FIG. 5: Effect of SEQ ID NO: 7 (4 or 40 nmol) on the recruitment of leukocytes and eosinophils in the brochoalveolar lavage in acute asthma. The bronchoalveolar lavage of mice was submitted for counting of the total number of cells (A) and eosinophils (B). The results represent the median±SEM of 6 animals/group. *$p<0.001$ compared to the Asthma group.

Treatment of animals presenting acute asthma, with 4 nmol or 40 nmol of the peptide tested, by all route of administration, provoked a decrease in the total number of leukocytes recruited to the alveolar space. This decrease was characterized by the absence of eosinophils, as can be verified in FIG. 5. The effect of the peptide tested on the recruitment of cells to the lung was similar to the effect induced by oral dexamethasone at a dose of 0.3 mg/Kg.

Figure 6:
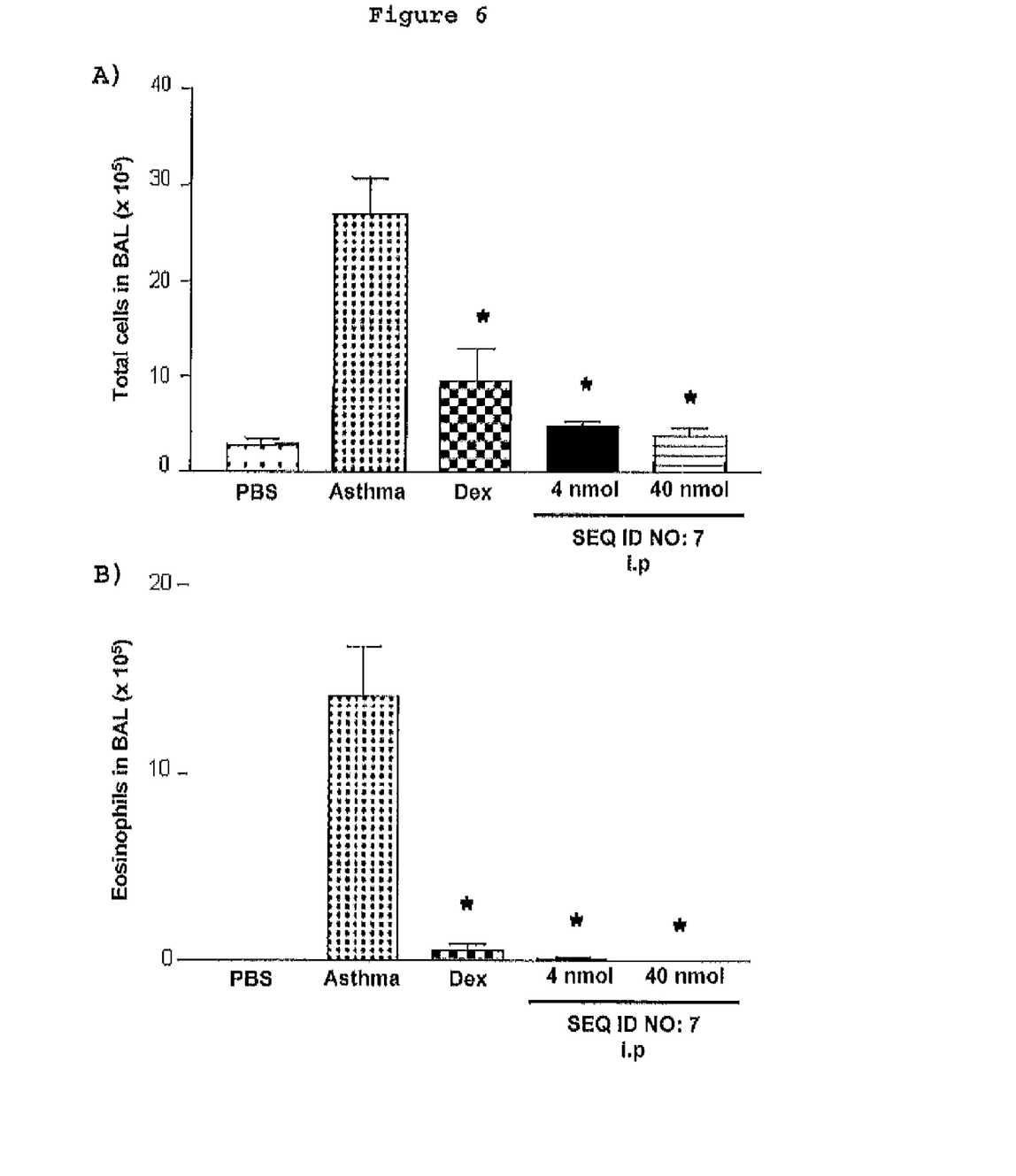
FIG. 6: Effect of SEQ ID NO: 7 on the recruitment of leukocytes and eosinophils in the bronchoalveolar lavage in chronic asthma. The bronchoalveolar lavage was submitted for counting of the total number of cells (A) and eosinophils (B). The results represent the median±SEM of 6 animals/group. *$p<0.001$ compared to the Asthma group.

Intraperitoneal treatment of animals presenting chronic asthma, with 4 nmol or 40 nmol of the peptide tested, provoked a decrease in the total number of leukocytes recruited to the alveolar space, with a decrease in eosinophils, as can be verified in FIG. 6. The effect of the peptide tested on recruitment of cells to the lung was similar to the effect induced by oral dexamethasone at a dose of 0.3 mg/Kg.

The invention claimed is:

1. A synthetic peptide consisting of 13 amino acids, presenting the amino acid cysteine at positions 4 and 13 and the amino acid lysine at position 11 of the peptide chain numbered from the N-terminal to C-terminal position, and a disulfide bridge from cysteine residues 4 to 13 that provides a cyclic structure, wherein the peptide possesses anti-inflammatory and/or anti-allergic activity and wherein the amino acid at position 1 is valine, leucine, isoleucine or another hydrophobic and neutral amino acid; the amino acid at position 3 is arginine, glutamine or another hydrophilic and polar amino acid; the amino acid at position 5 is arginine, threonine, serine, aspartate or another hydrophilic and polar amino acid; the amino acid at position 7 is methionine, isoleucine, leucine or another hydrophilic and neutral amino acid; the amino acid at position 9 is glycine or aspartate.

2. A peptide consisting of 13 amino acids, presenting the amino acid cysteine at positions 4 and 13, the amino acid lysine at position 11 of the peptide chain, and a disulfide bridge from cysteine residues 4 to 13 that provides a cyclic structure, said peptide having the amino acid sequence selected from the group consisting of:

| | |
|---|---|
| $Ile_1$-$Pro_2$-$Arg_3$-$Cys_4$-$Arg_5$-$Lys_6$-$Met_7$-$Pro_8$-$Gly_9$-$Val_{10}$-$Lys_{11}$-$Met_{12}$-$Cys_{13}$, | (SEQ ID NO: 1) |
| $Val_1$-$Glu_2$-$Gln_3$-$Cys_4$-$Thr_5$-$Ile_6$-$Ile_7$-$Gly_8$-$Asp_9$-$Glu_{10}$-$Lys_{11}$-$Asp_{12}$-$Cys_{13}$, | (SEQ ID NO: 2) |
| $Val_1$-$Glu_2$-$Gln_3$-$Cys_4$-$Thr_5$-$Ile_6$-$Ile_7$-$Gly_8$-$Asp_9$-$Ala_{10}$-$Lys_{11}$-$Asp_{12}$-$Cys_{13}$, | (SEQ ID NO: 3) |
| $Val_1$-$Gln_2$-$Gln_3$-$Cys_4$-$Ser_5$-$Glu_6$-$Ile_7$-$Ala_8$-$Gly_9$-$Ala_{10}$-$Lys_{11}$-$Pro_{12}$-$Cys_{13}$, | (SEQ ID NO: 4) |
| $Leu_1$-$His_2$-$Arg_3$-$Cys_4$-$Asp_5$-$Lys_6$-$Ile_7$-$Ala_8$-$Asp_9$-$Ala_{10}$-$Lys_{11}$-$Pro_{12}$-$Cys_{13}$, | (SEQ ID NO: 5) |
| $Ile_1$-$Pro_2$-$Arg_3$-$Cys_4$-$Arg_5$-$Ala_6$-$Met_7$-$Pro_8$-$Gly_9$-$Val_{10}$-$Lys_{11}$-$Met_{12}$-$Cys_{13}$, | (SEQ ID NO: 6) |
| $Ile_1$-$Pro_2$-$Arg_3$-$Cys_4$-$Arg_5$-$Lys_6$-$Met_7$-$Pro_8$-$Gly_9$-$Val_{10}$-$Lys_{11}$-$Met_{12}$-$Cys_{13}$-$NH_2$, | (SEQ ID NO: 7) |
| Ac-$Ile_1$-$Pro_2$-$Arg_3$-$Cys_4$-$Arg_5$-$Lys_6$-$Met_7$-$Pro_8$-$Gly_9$-$Val_{10}$-$Lys_{11}$-$Met_{12}$-$Cys_{13}$, and | (SEQ ID NO: 8) |
| Ac-$Ile_1$-$Pro_2$-$Arg_3$-$Cys_4$-$Arg_5$-$Lys_6$-$Met_7$-$Pro_8$-$Gly_9$-$Val_{10}$-$Lys_{11}$-$Met_{12}$-$Cys_{13}$-$NH_2$ | (SEQ ID NO: 9) | wherein the peptide possesses anti-inflammatory and/or anti-allergic activity.

3. The peptide according to claim 2 wherein the proline residues are individually, alternately or in conjunction substituted by hydroxyproline residues.

4. The peptide according to claim 2 wherein the methionine residues are individually, alternately or in conjunction substituted by residues of oxidized methionine.

5. The peptide according to claim 1 or claim 2, which is anti-asthmatic.

6. The peptide according to claim 1 or claim 2, which is an inhibitor of trypsin.

7. A pharmaceutical composition comprising a peptide of claim 1 or claim 2, alone or in a combination containing at least two of the peptides, or their pharmaceutically acceptable salts, and one or more pharmaceutically acceptable excipient, wherein the peptide is present in an effective quantity to treat acute and/or chronic inflammatory and/or allergic disorders.

8. A method to treat acute and/or chronic inflammatory and/or allergic disorders, comprising the step of administering, to a mammal, of an effective quantity of at least one of the peptides of claim 1.

9. The method, according to claim 8, wherein the peptide is orally, intranasally, intramuscularly or intravenously administered.

10. The method according to claim 8, wherein said disorder is at least one disorder selected from the group consisting of asthma, rhinitis, arthritis, atopic dermatitis and lymphocytic dysfunction during an immune response.

11. A synthetic peptide consisting of an amino acid sequence selected from the group consisting of:

Ile$_1$-Pro$_2$-Arg$_3$-Cys$_4$-Arg$_5$-Lys$_6$-Met$_7$-Pro$_8$-Gly$_9$-Val$_{10}$-Lys$_{11}$-Met$_{12}$-Cys$_{13}$, (SEQ ID NO: 1)

Val$_1$-Glu$_2$-Gln$_3$-Cys$_4$-Thr$_5$-Ile$_6$-Ile$_7$-Gly$_8$-Asp$_9$-Glu$_{10}$-Lys$_{11}$-Asp$_{12}$-Cys$_{13}$, (SEQ ID NO: 2)

Val$_1$-Glu$_2$-Gln$_3$-Cys$_4$-Thr$_5$-Ile$_6$-Ile$_7$-Gly$_8$-Asp$_9$-Ala$_{10}$-Lys$_{11}$-Asp$_{12}$-Cys$_{13}$, (SEQ ID NO: 3)

Val$_1$-Gln$_2$-Gln$_3$-Cys$_4$-Ser$_5$-Glu$_6$-Ile$_7$-Ala$_8$-Gly$_9$-Ala$_{10}$-Lys$_{11}$-Pro$_{12}$-Cys$_{13}$, (SEQ ID NO: 4)

Leu$_1$-His$_2$-Arg$_3$-Cys$_4$-Asp$_5$-Lys$_6$-Ile$_7$-Ala$_8$-Asp$_9$-Ala$_{10}$-Lys$_{11}$-Pro$_{12}$-Cys$_{13}$, (SEQ ID NO: 5)

Ile$_1$-Pro$_2$-Arg$_3$-Cys$_4$-Arg$_5$-Ala$_6$-Met$_7$-Pro$_8$-Gly$_9$-Val$_{10}$-Lys$_{11}$-Met$_{12}$-Cys$_{13}$, (SEQ ID NO: 6)

Ile$_1$-Pro$_2$-Arg$_3$-Cys$_4$-Arg$_5$-Lys$_6$-Met$_7$-Pro$_8$-Gly$_9$-Val$_{10}$-Lys$_{11}$-Met$_{12}$-Cys$_{13}$-NH$_2$, (SEQ ID NO: 7)

Ac-Ile$_1$-Pro$_2$-Arg$_3$-Cys$_4$-Arg$_5$-Lys$_6$-Met$_7$-Pro$_8$-Gly$_9$-Val$_{10}$-Lys$_{11}$-Met$_{12}$-Cys$_{13}$, (SEQ ID NO: 8)

Ac-Ile$_1$-Pro$_2$-Arg$_3$-Cys$_4$-Arg$_5$-Lys$_6$-Met$_7$-Pro$_8$-Gly$_9$-Val$_{10}$-Lys$_{11}$-Met$_{12}$-Cys$_{13}$-NH$_2$, and (SEQ ID NO: 9)

Cys$_1$-Arg$_2$-Lys$_3$-Met$_4$-Pro$_5$-Gly$_6$-Val$_7$-Lys$_8$-Met$_9$-Cys$_{10}$, (SEQ ID NO: 12)

wherein the peptide includes a disulfide bridge between cysteine residues that provides a cyclic structure, and possesses anti-inflammatory and/or anti-allergic activity.

12. A method to treat acute and/or chronic asthma, comprising the step of administering to a mammal an effective quantity of at least one of the peptides of claim 11.

13. A method to treat acute and/or chronic inflammatory and/or allergic disorders, comprising the step of administering, to a mammal, of an effective quantity of at least one of the peptides of claim 2.

14. The method, according to claim 13, wherein the peptide is orally, intranasally, intramuscularly or intravenously administered.

15. The method according to claim 13, wherein said disorder is at least one disorder selected from the group consisting of asthma, rhinitis, arthritis, atopic dermatitis, and lymphocytic dysfunction during an immune response.

* * * * *